(12) United States Patent
Smits et al.

(10) Patent No.: US 9,428,497 B2
(45) Date of Patent: Aug. 30, 2016

(54) PRECURSOR COMPOUNDS FOR THE RADIOSYNTHESIS OF [¹⁸F] NORCHLORO-FLUOROHOMOEPIBATIDINE

(75) Inventors: René Smits, Dresden (DE); Alexander Hoepping, Dresden (DE); Steffen Fischer, Leipzig (DE); Achim Hiller, Markranstaedt (DE); Winnie Deuther-Conrad, Leipzig (DE); Peter Brust, Leipzig (DE); Jörg Steinbach, Bischofswerda (DE); Marianne Patt, Leipzig (DE); Jörg Thomas Patt, Leipzig (DE); Osama Sabri, Leipzig (DE)

(73) Assignees: ABX ADVANCED BIOCHEMICAL COMPOUNDS GMBH, Radeberg (DE); HELMHOLTZ-ZENTRUM DRESDEN-ROSSENDORF E.V., Dresden (DE); UNIVERSITAET LEIPZIG, Leipzig (DE)

( * ) Notice: Subject to any disclaimer, the term of this patent is extended or adjusted under 35 U.S.C. 154(b) by 24 days.

(21) Appl. No.: 14/236,801

(22) PCT Filed: Jul. 31, 2012

(86) PCT No.: PCT/EP2012/064930
§ 371 (c)(1),
(2), (4) Date: May 15, 2015

(87) PCT Pub. No.: WO2013/017585
PCT Pub. Date: Feb. 7, 2013

(65) Prior Publication Data
US 2015/0259338 A1 Sep. 17, 2015

Related U.S. Application Data

(60) Provisional application No. 61/591,341, filed on Jan. 27, 2012.

(30) Foreign Application Priority Data

Aug. 1, 2011 (DE) ........................ 10 2011 052 348

(51) Int. Cl.
C07D 451/00 (2006.01)
C07D 451/04 (2006.01)
C07D 451/02 (2006.01)

(52) U.S. Cl.
CPC .................. C07D 451/02 (2013.01)

(58) Field of Classification Search
CPC ............................ C07D 451/00; C07D 451/04
USPC ........................................................ 546/124
See application file for complete search history.

(56) References Cited

FOREIGN PATENT DOCUMENTS

WO 2013017585 A1 2/2013

OTHER PUBLICATIONS

J. Label Compd. Radiopharm., vol. 46, Jan. 1, 2003, pp. S1-S403, XP55036668, cited in the application p. S168.

Y.-S. Ding: "Synthesis of [18F] Norchlorofluoroepibatidine and its N-methyl Derivative: New PET Ligands for Mapping Nicotinic Acetylcholine Receptors", Journal of Labelled Compounds and Radiopharmaceutcials, vol. 39, No. 10, Jan. 1, 1997, pp. 827-832, XP55036729, Scheme 1; pp. 828-830.
Feng Lian: "Synthesis and Nicotinic Acetylcholine Receptor Binding Properties of exo-2-(2-Fluoro-5-Pyridinyl)-7-azabicyclo- [2.2.1] heptane: A New Positron Emission Tomography Ligand for Nicotinic Receptors", Journal of Medicinal Chemistry, vol. 40, No. 15, Jan. 1, 1997, pp. 2293-2295, XP55036725, Scheme I.
Brust, P., et al. (2008). In Vivo Measurement of Nicotinic Acetylcholine Receptors with [18F]Norchloro-Fluoro-Homoepibatidine. Synapse, 62(3), 205-218. Retrieved from http://www.ncbi.nlm.nih.gov/pubmed/18088060.
Nordberg, A. (2001). Nicotinic Receptor Abnormalities of Alzheimer's Disease: Therapeutic Implications. Society of Biological Psychiatry, 49(3), 200-210. Retrieved from http://www.ncbi.nlm.nih.gov/pubmed/11230871.
Sabbagh, M. et al., (2006). Pathologic and Nicotinic Receptor Binding Differences between Mild Cognitive Impairment, Alzheimer Disease, and Normal Aging. Archives of Neurology, 63(12), 1771-1776. Retrieved from http://www.ncbi.nlm.nih.gov/pubmed/17172618.
Sabri, O. et al., (2008). Acetylcholine Receptors in Dementia and Mild Cognitive Impairment. European Journal of Nuclear Medicine and Molecular Imaging, 35(1), 30-45. doi: 10.1007/s00259-007-0701-1.
O'Brien, J. et al., (2006). α4β2 Nicotinic Receptor Status in Alzheimer's Disease Using I-51a-85380 Single-Photon-Emission Computed Tomography. Journal of Neurology, Neurosurgery & Psychiatry, 78(4), 356-362. Retrieved from hftp://www.ncbi.nlm.nih.gov/pubmed/1713546.
Malpass, J., et al. (2001). Synthesis and Nicotinic Acetylcholine-Binding Properties of Epibatidine Homologues: Homoepibatidine and Dihomoepibatidine. Journal of the Chemical Society, Perkin Transactions 1,1(9), 1044-1050. doi: 10.1039/B010178H.
International Search Report in PCT/EP/2012/064930 dated Sep. 5, 2012.
IPRP in PCT/EP/2012/064930 dated Feb. 4, 2014.
Japanese Office Action dated Nov. 25, 2015, in connection with JP Application No. 2014-523301 (English translation only, 3 pgs.).
Jikkenn Kgaku Kouza 20 Yukigaousei II (Guidebook for Chemical Experiment 20, Organic Synthesis II 4th ed.), 1992, pp. 284-288 (5 pgs.).
Chinese Office Action dated Jan. 5, 2016, in connection with corresponding Chinese Application No. 201280038110.6 (9 pgs., English translation only).

*Primary Examiner* — Niloofar Rahmani
(74) *Attorney, Agent, or Firm* — Maier & Maier, PLLC

(57) ABSTRACT

The invention relates to a compound of formula Ia or Ib wherein $R^1$ represents $-CO_2R^3$, $-COR^4$ or $-R^5$, wherein $R^3$ represents unsubstituted or substituted $C_1$-$C_6$ alkyl, $R^4$ represents hydrogen, unsubstituted or substituted $C_1$-$C_6$ alkyl, and $R^5$ represents hydrogen, unsubstituted or substituted $C_1$-$C_6$ alkyl, $R^2$ represents $-N^+(R^6)(R^7)(R^8)X^-$ or a nitro group, wherein $R^6$, $R^7$, $R^8$ independently of each other represent unsubstituted or substituted $C_1$-$C_6$ alkyl or unsubstituted or substituted $-(CH_2)n-$ with n=1 to 12 provided that at least two of the substituents $R^6R^7R^8$ are $C_1$-$C_6$ alkyl, and $X^-$ represents a halide, sulphonate, unsubstituted or substituted acetate, sulphate, hydrogen sulphate, nitrate, perchlorate, or oxalate.

5 Claims, No Drawings

US 9,428,497 B2

PRECURSOR COMPOUNDS FOR THE RADIOSYNTHESIS OF [$^{18}$F] NORCHLORO-FLUOROHOMOEPIBATIDINE

RELATED APPLICATIONS

This application is the U.S. national stage application under 35 U.S.C. §371 of International Patent Application No. PCT/EP2012/064930, filed on Jul. 31, 2012, which claims priority under 35 U.S.C. §119, to German Patent Application No. 10 2011 052 348.0, filed Aug. 1, 2011, the disclosure of which is incorporated herein by reference in their entireties.

The invention relates to precursor compounds for the radiosynthesis of the enantiomerically pure, nicotinic acetylcholine receptor ligands (−)-[$^{18}$F]norchloro-fluoro-homoepibatidine and (+)-[$^{18}$F]norchloro-fluoro-homoepibatidine. Further, it relates to a method for the preparation of said precursor compounds as well as uses of said precursor compounds.

(−)-[$^{18}$F]norchloro-fluoro-homoepibatidine, in the following referred to as (−)-[$^{18}$F]NCFHEB, and (+)-[$^{18}$F] norchloro-fluoro-homoepibatidine, in the following referred to as (+)-[$^{18}$F]NCFHEB, are suitable PET radiotracers for the nuclear-medical diagnostics in animal experiments (*Synapse* 2008, 62, 205-18). Positron emission tomography (PET) is a standard method of the nuclear-medical imaging diagnostics and is in particular employed in the oncology and neurology and here, i. a. in the diagnosis of dementias.

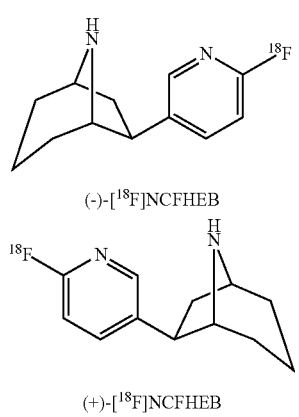

(−)-[$^{18}$F]NCFHEB (+)-[$^{18}$F]NCFHEB

More than the half of dementias is caused by Alzheimer's disease (AD). A definite diagnosis of AD is only possible in the stage of dementia, that is, if already severe cognitive symptoms are present. While cholinergic marker enzymes are probably significantly reduced only in advanced disease stages of AD, pathological studies lead to assume that a reduction of nicotinic acetylcholine receptors is a specific and early event in AD (*Biol. Psychiatry* 2001, 49, 200-210, *Arch Neurol* 2006, 63, 1771-6). Up to now, only a few clinical imaging studies have shown nicotinic acetylcholine receptors by means of Single-Photon Emission Computer Tomography (SPECT) or PET (*Eur J Nucl Med Mol Imaging* 2008, 35 *Suppl* 1, S30-45, *J Neurol Neurosurg Psychiatry* 2007, 78, 356-62). However, the radioligands used in these studies either show a high unspecific binding or are methodically ill-suited to absolutely quantify nicotinic acetylcholine receptors. Studies with 2-[$^{18}$F]F-A85380 in patients having neurodegenerative diseases, inter alia AD and preliminary stages of AD, so-called mild cognitive disorders (MCD), show an early reduction of nicotinic acetylcholine receptors already in the stage of MCD and lead to assume a statement in view of the prognosis of the patients. However, the use of the conventional radiotracer (2-[$^{18}$F]F-A-85380) for the neuroimaging of nicotinic acetylcholine receptors in patients requires a 7-hour acquisition time which makes the radiotracer unsuitable for routine clinical PET studies. In initial preclinical studies the new radioligand (−)-[$^{18}$F]NCFHEB has a cerebral uptake that is by more than two times higher in mice and piglets than that of 2-[$^{18}$F]F-A-85380 (*Synapse* 2008, 62, 205-18). PET studies in piglets have shown that (−)-[$^{18}$F]NCFHEB has a significantly much faster binding kinetics in the brain than 2-[$^{18}$F]F-A-85380. Thus, this faster kinetics should permit the clinical employment of (−)-[$^{18}$F]NCFHEB as a first potential diagnostic early marker of AD. Possibly, by means of (−)-[$^{18}$F]NCFHEB prognostic statements can be made already in the stage of pre-dementia. Moreover, by means of (−)-[$^{18}$F]NCFHEB PET an in vivo imaging to assess new therapy approaches would be available.

According to the state of the art the synthesis of (−)-[$^{18}$F] NCFHEB starts with the racemic bromo precursor the tropane nitrogen of which is protected as ethyl carbamate. The synthesis is carried out using a microwave. After radiosynthesis the enantiomers are separated via a chiral HPLC. This is followed by a second HPLC on a reversed phase to finally purify the product. The radiochemical yield is approx. 2%. (*J. Lab. Comp. Radpharm.* 2003, 46, 168, *Synapse* 2008, 62, 205).

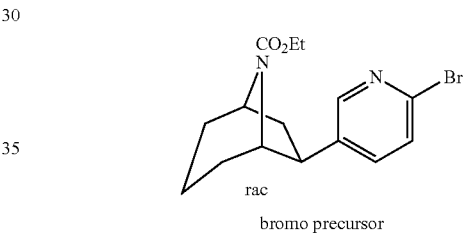

bromo precursor

The low overall yield and the costly purification make the commercial use of said precursor unlikely and complicate the preparation of the corresponding F-18 compounds (s. compounds 1 and 2) for clinical use.

Object of the invention is to eliminate the drawbacks of the prior art. In particular, there are provided compounds that allow a simpler preparation of (−)-[$^{18}$F]NCFHEB and (+)-[$^{18}$F]NCFHEB. Furthermore, a method for the preparation of said compounds as well as the uses of said compounds in the radiosynthesis are provided.

This object is solved by the features of the invention. Practical embodiments of the inventions are provided herein.

According to the invention there is provided a compound of formula Ia or Ib

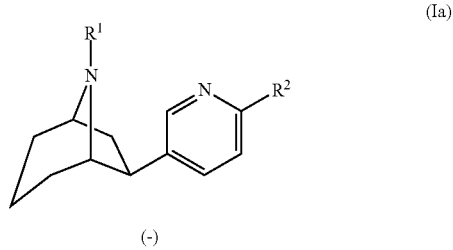

(Ia)

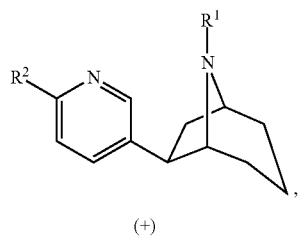

(Ib)

wherein
R¹ represents —CO₂R³, —COR⁴ or —R⁵, wherein
  R³ represents unsubstituted or substituted $C_1$-$C_6$ alkyl,
  R⁴ represents hydrogen, unsubstituted or substituted $C_1$-$C_6$ alkyl, and
  R⁵ represents hydrogen, unsubstituted or substituted $C_1$-$C_6$ alkyl,
R² represents —N⁺(R⁶)(R⁷)(R⁸)X⁻ or a nitro group, wherein
  R⁶, R⁷, R⁸ independently of each other represent unsubstituted or substituted $C_1$-$C_6$ alkyl or unsubstituted or substituted —(CH₂)$_n$— with n=1 to 12 provided that at least two of the substituents R⁶, R⁷, and R⁸ are $C_1$-$C_6$ alkyl, and
  X⁻ represents a halide, sulphonate, unsubstituted or substituted acetate, sulphate, hydrogen sulphate, nitrate, perchlorate, or oxalate.

The compounds of formula Ia and Ib are precursors for the preparation of the radiotracers (−)-[¹⁸F]NCFHEB (compound of formula Xa) and (+)-[¹⁸F]NCFHEB (compound of formula Xb), respectively. In using the compounds of formula Ia and Ib as precursors yields of these radiotracers of more than 70% and with a high chemical and radiochemical purity are obtained. The employment of the enantiomerically pure precursor of formula Ia eliminates the time-consuming separation of the enantiomers and the compound of formula Xa can be prepared sterile in a short overall synthesis time with a high specific activity (>350 GBq/μmol) and high activity (up to 400 GBq) for diagnostic PET studies.

The term "$C_1$-$C_6$ alkyl" relates to straight-chain or branched, saturated, aliphatic hydrogen carbon groups with 1 to 6 carbon atoms. Examples of $C_1$-$C_6$ alkyl groups are methyl, ethyl, n-propyl, iso-propyl, n-butyl, iso-butyl, sec-butyl, and tert-butyl, n-pentyl, n-hexyl.

The term "substituted $C_1$-$C_6$ alkyl" relates to $C_1$-$C_6$ alkyl, as defined above, having one or more substituents selected from the group consisting of NH₂, NH($C_1$-$C_4$ alkyl), N($C_1$-$C_4$ alkyl)₂, halogen, $C_1$-$C_4$ alkyl, OH, O($C_1$-$C_4$ alkyl), NO₂, CN, CO₂H, or CO₂($C_1$-$C_4$ alkyl), wherein each of the preceding $C_1$-$C_4$ alkyl groups is unsubstituted or substituted with at least one halogen atom.

The term "unsubstituted or substituted —(CH₂)$_n$— with n=1 to 12" relates to a straight-chain carbon chain of 1 to 12 methylene units (CH₂) that is completely saturated and has a first linkage to the ammonium nitrogen atom of the N⁺(R⁶)(R⁷)(R⁸)X⁻ group and a second linkage to a solid phase. At least one of the methylene units may be substituted, for example with at least one halogen atom. For example, one or all of the methylene units may be perfluorinated.

Examples of a solid phase are materials having a solid or semi-solid surface such as for example resins, polymers, glass, or other surfaces.

The term "nitro" relates to the group NO₂ bonded to a carbon atom.

The term "halide" relates to chloride, bromide, and iodide.

The term "halogen" relates to fluorine, chlorine, bromine, and iodine.

The radicals halide, sulphonate, acetate, sulphate, hydrogen sulphate, nitrate, perchlorate, and oxalate given for X⁻ each designate the anionic group of the corresponding salt. If the anionic group is bi or multivalent, so the cation is present in an amount which corresponds to the valence of the anionic group.

The term "sulphonate" relates to salts of the sulphonic acids of the general formula R⁹—SO₃⁻, wherein R⁹ may present a halogen-substituted or unsubstituted $C_1$-$C_6$ alkyl group or a substituted aryl group. Examples of sulphonates are mesylate (R⁹=CH₃), triflate (R⁹=CF₃), and tosylate (R⁹=4-methylphenyl).

The term "substituted acetate" relates to halogenated acetates of the general formula (R¹⁰)(R¹¹)(R¹²)—CCO—, wherein R¹⁰, R¹¹, R¹² are halogens. Examples of substituted acetates are trifluoroacetate (R¹⁰=R¹¹=R¹²=F) and trichloroacetate (R¹⁰R¹¹=R¹²=Cl).

Preferably, R³ is selected from the group consisting of methyl, ethyl, tert-butyl, (9H-fluorenyl)methyl, allyl, and benzyl. More preferably R³ is tert-butyl.

R⁴ is preferably selected from the group consisting of hydrogen, methyl, and trifluoromethyl. Particularly preferred R⁴ is methyl.

Preferably, R⁵ is selected from the group consisting of benzyl, methoxybenzyl, dimethoxybenzyl, allyl, diphenyl, and trityl. Particularly preferred R⁵ is trityl.

Preferably, R⁶, R⁷, R⁸ are independently selected from the group consisting of methyl, ethyl, and tert-butyl. Preferably, R⁶, R⁷, R⁸ are methyl.

X⁻ is preferably selected from the group consisting of chloride, bromide, iodide, mesylate, and triflate. Particularly preferred is iodide.

A preferred compound is (−)-5-(8-(tert-butoxycarbonyl)-8-azabicyclo[3.2.1]octane-6-yl)-N,N,N-trimethylpyridine-2-aminium iodide (compound of formula Ia-1)

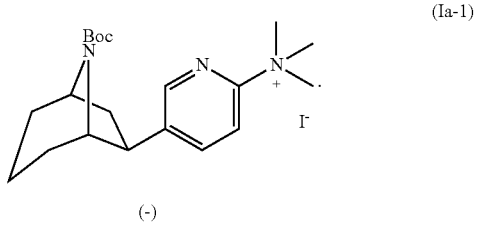

(Ia-1)

According to the present invention there is further provided a method for the preparation of a compound of formula Ia, the method comprising at least one of the following steps. Preferably, the method comprises at least steps 1, 2, and 3 in the given order. More preferably, the method comprises at least steps 1, 2, 3, 4, 5, and 6 in the given order.

The skilled person will readily recognize that the procedure described can analogically be applied to the synthesis of a compound of formula Ib with the only difference that step 5 starts with a compound of formula VI instead of a compound of formula V and then, in step 6 the reaction product of this changed step 5 is employed.

Synthesis of the compound of formula Ia-1, which is a (−)-[¹⁸F]NCFHEB precursor, is shown in scheme 1 below. Compound Ia-1 is a compound coming under the general formula Ia.

Scheme 1: Synthesis of the (-)-[$^{18}$F]NCFHEB precursor Ia-1.

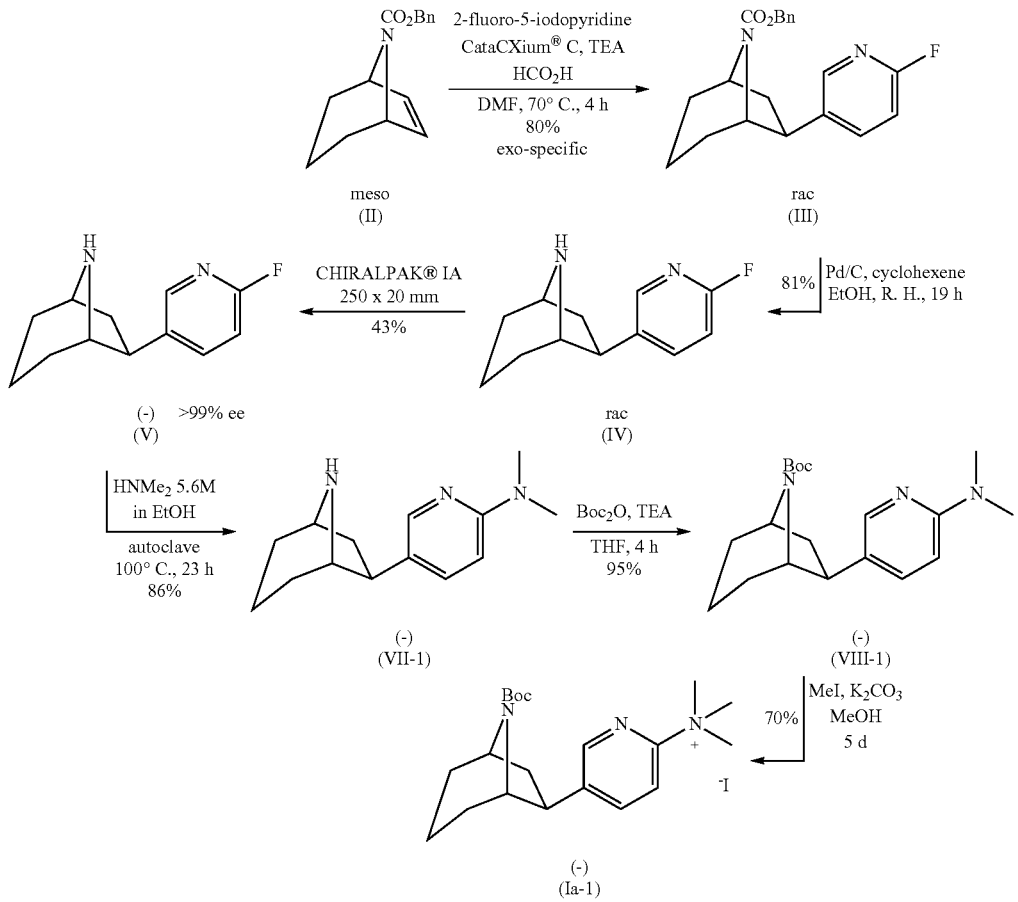

Step 1

The method according to the invention can comprise the reaction of a compound of formula II

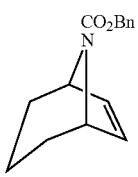

(II)

with 2-fluoro-5-iodopyridine using a palladium catalyst to a compound of formula III

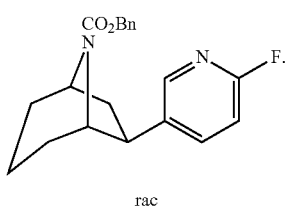

(III)

The method includes the reaction of a compound of formula II provided with a benzyloxycarbonyl protective group. Compounds of this type are available to the skilled person by known syntheses from literature (*J. Chem. Soc., Perkin Trans.* 1, 2001, 1044). The use of the benzyloxycarbonyl protective group allows an efficient synthesis of the parent compound of formula II and cleaving-off of the protective group under mild hydrogenolytic conditions.

Preferably, the compound of formula II is converted by a reductive Heck coupling to the racemic compound of formula III. Suitable palladium catalysts for the exo-specific introduction of the pyridine substituent are palladium(II) acetate, tetrakis(triphenylphosphine)palladium, bis(triphenylphosphine)-palladium(II)diacetate, and trans-di(μ-acetate)bis[o-(di-o-tolyl-phosphine)benzyl]dipalladium(II) (CataCXium® C), with trans-di(μ-acetate)bis[o-(di-o-tolyl-phosphine)benzyl]dipalladium(II) being preferred. A commercially available example of trans-di(μ-acetate)bis[o-(di-o-tolyl-phosphine)benzyl]dipalladium(II) is "CataCXium® C" (trade name, marketed by Sigma-Aldrich Co., St. Louis, US.)

Step 2

The method according to the invention may further comprise the cleavage of the protective group in a compound of formula III with hydrogen using a palladium catalyst to obtain a compound of formula (IV)

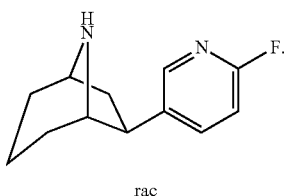

(IV)

rac

Therefore, this process step includes a hydrogenolytic cleavage of the protective group from the compound of formula III to obtain the compound of formula IV. The cleavage of this protective group is of advantage because the free amine can be effectively separated into the individual enantiomers by chiral HPLC using a chiral stationary phase.

Step 3

Further, the method according to the invention may include an enantiomeric separation of the compound of formula IV to obtain the compounds of formula V and/or formula VI

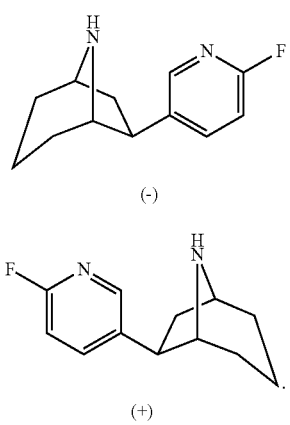

(V)
(-)

(VI)
(+)

Here, the compounds of formula V and VI are obtained separated from each other. The enantiomeric separation may be performed by enantioselective phases known to the person skilled in the art such as Brush, helical polymers, cyclodextrines, or crown ethers, or by ligand exchange phases, proteins, macrocyclic ligand exchange phases, carbon or ceramic based phases. Preferably, the enantiomeric separation is done using a chiral stationary phase. One example of a suitable and commercially available chiral stationary phase is the Chiralpak® IA phase (trade name of Daicel Chemicals Industries Ltd, JP). A preferred mobile solvent is acetonitrile/0.1% diethylamine.

The thus obtained enantiomers are (−)-norchloro-fluoro-homoepibatidine (compound of formula V), also referred to as (−)-NCFHEB, and (+)-norchloro-fluoro-homoepibatidine (compound of formula VI), also referred to as (+)-NCFHEB. (−)-NCFHEB can be used as starting material for the synthesis of the enantiomerically pure precursor of formula Ia-1. Furthermore, (−)-NCFHEB may be used as cold reference standard in the radiosynthesis.

(+)-NCFHEB may be used as the starting material for the synthesis of the enantiomerically pure precursor of formula Ib-1. Furthermore, (+)-NCFHEB may be used as cold reference standard in the radiosynthesis

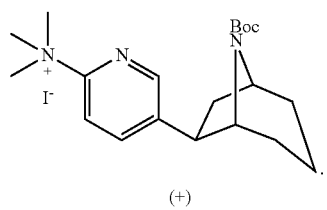

(Ib-1)
(+)

Step 4

Moreover, the method according to the invention may comprise the substitution of the fluorine in a compound of formula V with a dialkylamine to obtain a compound of formula VII,

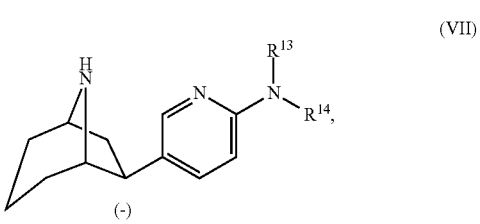

(VII)
(-)

wherein $R^{13}$ and $R^{14}$ are independently selected from the group consisting of methyl, ethyl, and propyl. Preferably, $R^{13}$ and $R^{14}$ are methyl. Here, the dialkylamine is of the general formula $(R^{13}R^{14})NH$.

Preferably, the reaction is carried out using dimethylamine hydrochloride and potassium carbonate in dimethyl sulphoxide at 100° C. More preferably, the synthesis is carried out by heating the compound of formula V in a solution of dimethylamine in ethanol in an autoclave.

Step 5

Additionally, the method according to the invention may comprise the introduction of a protective group into the compound of formula VII to obtain a compound of formula VIII

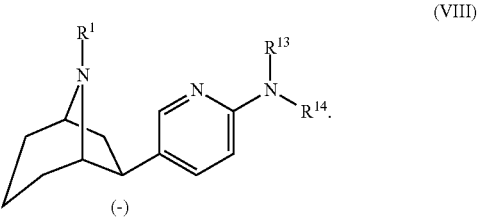

(VIII)
(-)

The compounds of formula VII cannot readily be quaternized. Thus, before the final quaternization the nitrogen on the tropane ring should again be provided with a protective group that is also suitable for radiosynthesis, whereby a compound of formula VIII is obtained.

Step 6

Additionally, the method according to the invention may comprise the quaternization of the compound of formula VIII with an alkylating agent to a compound of formula Ia. A preferred alkylating agent is methyl iodide.

The choice of the alkylating agent is decisive for the success of the reaction. Typically, in the prior art it is alkylated with methyl iodide or methyl triflate. As has now been surprisingly found the use of methyl triflate is not suitable for the preparation of the trimethyl ammonium salts because a number of by-products is generated due to the high reactivity of said alkylating agent. Only by the use of methyl iodide the target compound Ia-1 is obtained in a high yield and a very good purity. The counter anion of compound Ia-1 can be replaced by methods known to those of skill in the art.

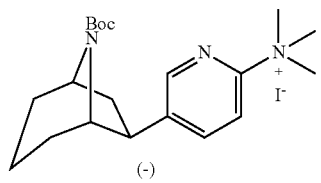

(Ia-1)

Compound Ia-1 is a compound coming under the general formula Ia.

According to the present invention there is further provided the use of a compound of formula Ia for the preparation of a compound of formula IXa

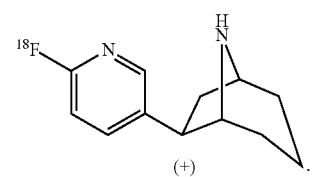

(IXa)

The method for the preparation of compound IXa preferably comprises at least one of steps 7 and 8. Preferably, the method comprises steps 7 and 8 in the given order.

Those of skill in the art will readily recognize that the procedure described can analogously be applied to the synthesis of (+)-[$^{18}$F]NCFHEB with the only difference that a compound of formula Ib is used for the preparation of compound IXb

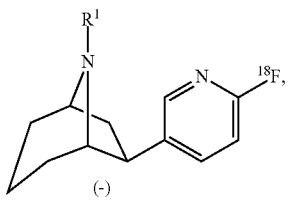

(IXb)

Scheme 2: Radiochemical Synthesis of (-)-[$^{18}$F]NCFHEB with precursor Ia-1

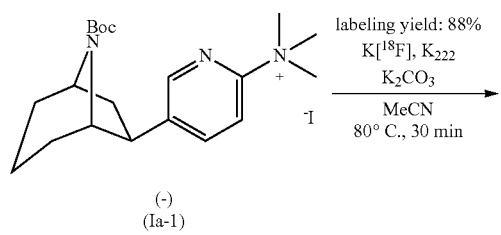

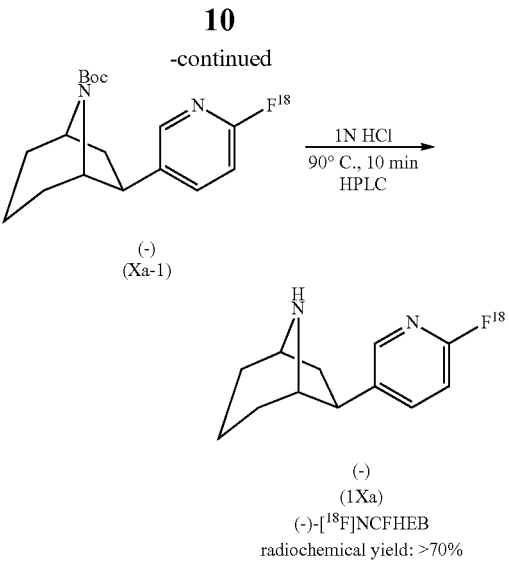

Step 7

A compound of formula Ia is converted to a compound of formula Xa

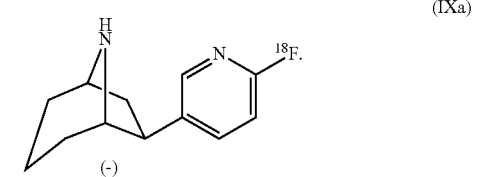

(Xa)

wherein R$^1$ represents —CO$_2$R$^3$, —COR$^4$, or —R$^5$, wherein
  R$^3$ represents unsubstituted or substituted C$_1$-C$_6$ alkyl,
  R$^4$ represents hydrogen, unsubstituted or substituted C$_1$-C$_6$ alkyl; and
  R$^5$ represents unsubstituted or substituted C$_1$-C$_6$ alkyl.

In step 7 the compounds of formula Ia are converted into the corresponding fluorinated compounds of formula Xa in a nucleophilic fluorination with $^{18}$F-fluoride. Typically, $^{18}$F-fluoride is prepared in the cyclotron by irradiation of 98% enriched H$_2$$^{18}$O with protons of an energy of 16 MeV. The aqueous $^{18}$F-fluoride solution obtained in this way is directly transferred to an organic solvent (preferably MeCN) wherein defined amounts of a phase transfer catalyst (PTC) such as crown ethers or quaternary ammonium salts as well as alkali or alkaline earth salts are dissolved. As the PTC preferably a [2,2,2]-cryptand (Kryptofix® or K222) or tetrabutylammonium hydroxide or optionally other crown ethers like 18-C-6 are used. Preferably, the $^{18}$F labeling is carried out under thermal reaction in the closed reaction vessel at an elevated temperature. With reaction times of less than 30 minutes high labeling yields and as a rule only a few radioactive by-products are obtained.

$^{18}$F Labeling can also be performed as a microwave-based reaction. For that, microwaves with a power of 50 to 150 W, preferably 75 to 85 W are radiated onto a special closed reaction vessel.

For determining the labeling yield and radioactive by-products thin layer chromatography (TLC) and high performance liquid chromatography (HPLC) may be used.

Step 8

A compound of formula Xa is reacted with an acid to a compound of formula IXa

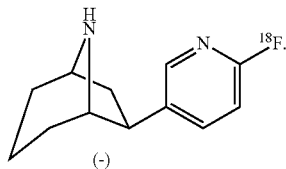

(IXa)

Preferably, the acid is a diluted acid. Examples of diluted acids are mineral acids such as hydrochloric or phosphoric acid, organic acids such as acetic acid or oxalic acid.

Subsequent to the $^{18}$F labeling made in step 7, in step 8 there is performed the cleavage of the protective groups from the $^{18}$F intermediates according to conventional methods, but preferably by optimized new procedures. Here, the reagent for the cleavage (cleavage solution) is added to the batches as an aqueous solution, which makes it possible to carry out the reaction in particular with the water-miscible solvents MeCN, DMF, or DMSO. The use of molar solutions of acids and bases, respectively, and elevated temperatures of 80° C. to 100° C., preferably 100° C., result in high conversions in short reaction times. In addition to trifluoroacetic acid (TFA) that is known to those of skill in the art organic acids such as 20% acetic acid or oxalic acid, but in particular inorganic acids such as 0.5-1M hydrochloric or 0.5-1N phosphoric acid may be used as acidic cleavage solution. As basic cleavage solution 0.5-1N sodium hydroxide solution is preferred.

Subsequently, for cleaning up the reaction product preferably solid phase extraction (SPE) using RP phases or ion exchange resins may be used as cartridge technique. Particularly well proven have cartridges of C18 phases conditioned with ethanol such as Sep-Pak C18 Plus (Waters, USA) or mixed mode phases with cation exchanger and RP functions such as OASIS MCX (Waters, USA).

It is better to directly subject the aqueous reaction solution (after cleavage of the protective group) to a semi-preparative HPLC, wherein separations on conventional C18 reverse chases with buffered aqueous organic eluents, optionally in an acidic, neutral, or basic milieu, guarantee a high separation performance and highly pure product solutions.

In this way, the radiotracer (−)-[$^{18}$F]NCFHEB (compound of formula IXa) is obtained in yields of more than 70% in a high chemical and radiochemical purity. The use of the chiral precursor of formula Ia eliminates the time-consuming separation of the enantiomers and the compound can be prepared sterile in a short overall synthesis time with a high specific activity (>350 GBq/μmol) and high activity (up to 400 GBq) for diagnostic PET studies.

Hereinafter, the invention is explained in more detail with the help of examples which are not intended to limit the invention.

EXAMPLES

The abbreviations used have the following meaning:
Boc=tert-butyloxycarbonyl
Boc$_2$O=di-tert-butyl dicarbonate
DCM=dichloromethane
DMAP=4-(N,N-dimethylamino)pyridine
DMF=N,N-dimethylformamide
EE=acetic ester (ethylacetate)
EtOH=ethanol
eq=equivalent
FMOC—Cl=fluorenyloxycarbonylchloride
HCl=hydrochloric acid
Hex=hexane
HNMe$_2$=dimethylamine
HPLC=high performance liquid chromatography
K222=1,10-diaza-4,7,13,16,21,24-hexaoxabicyclo[8.8.8]hexacosane
K$_2$CO$_3$=potassium carbonate
MeCN=acetonitrile
MeI=methyl iodide
MeOH=methanol
Pd/C=palladium on activated carbon
PE=petroleum ether
PTC=phase transfer catalysis
RT=room temperature
TEA=triethylamine
THF=tetrahydrofuran Example 1

Preparation of (+/−)-exo-6-(6-Fluoro-pyridine-3-yl)-8-aza-bicyclo[3.2.1]octane-8-carboxylic acid benzyl ester (III)

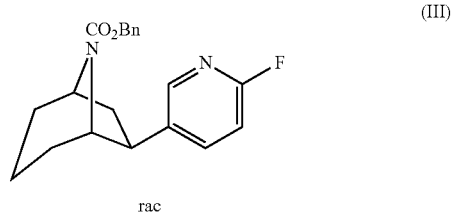

(III)

7.79 g (32 mmol, 1 eq) of meso-8-aza-bicyclo[3.2.1]oct-6-en-8-carboxylic acid benzyl ester (II) are dissolved in 73 ml of DMF. 15.5 ml of TEA (112 mmol, 3.5 eq) and 17.9 g (80 mmol, 2.5 eq) of 2-fluoro-5-iodopyridine are added. The solution is placed under argon and 1.8 g (1.92 mmol, 6 mol %) of trans-bis(acetato)bis[o-(di-o-tolylphosphino)benzyl]-dipalladium(II) is added. Finally, 3.2 ml (84.9 mmol, 2.65 eq) of formic acid are added. The reaction mixture is stirred for 4 h at 70° C. After cooling to RT it is filtered over celite and washed with EE. It is diluted with EE and H$_2$O, the phases are separated, and the aqueous phase is extracted twice with EE. The combined organic phases are dried over sodium sulphate and the solvent is removed in vacuo. The crude product is purified by column chromatography (EE: hex=1:5). 8.78 g (25.8 mmol, 80%) of a light brown solid is obtained.

$^1$H-NMR (CDCl$_3$, 500 MHz) two rotameric forms (RotA/RotB) result in a doubling of some signals: δ=7.98-8.04 (m, 1H, RotA, 1H, RotB), 7.59 (ddd, J=8.1 Hz, 5.6 Hz, 2.5 Hz, 1H, RotB), 7.53 (ddd, J=8.1 Hz, 5.6 Hz, 2.5 Hz, 1H, RotA), 7.27-7.43 (m, 5H, RotA, 5H, RotB), 6.82 (dd, J=8.5 Hz, 2.9 Hz, 1H, RotB), 6.75 (dd, J=8.5 Hz, 2.9 Hz, 1H, RotA), 5.16-5.24 (m, 1H, RotA, 2H, RotB), 5.13 (d, J=12.4 Hz, 1H, RotA), 4.53 (bd, J=7.3 Hz, 1H, RotA), 4.46 (bd, J=7.2 Hz, 1H, RotB), 4.22 (bs, 1H, RotB), 4.13 (bs, 1H, RotA), 3.20-3.27 (m, 1H, RotA, 1H, RotB), 2.26-3.36 (m, 1H, RotA, 1H, RotB), 1.58-1.99 (m, 6H, RotA, 6H, RotB), 1.48-1.58 (m, 1H, RotA, 1H, RotB).

Example 2

Preparation of (+/−)-6-(6-Fluoro-pyridine-3-yl)-8-aza-bicyclo[3.2.1]octane (IV)

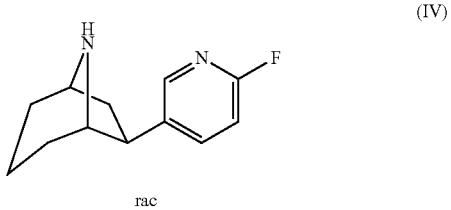 [SMILES: Fc1ccc(C2CC3CCCC2N3)cn1]

10.5 g (30.8 mmol, 1 eq) of (+/−)-exo-6-(6-fluoro-pyridine-3-yl)-8-aza-bicyclo[3.2.1]octane-8-carboxylic acid benzyl ester (III) are stirred in 140 ml of cyclohexene and 280 ml of ethanol until complete dissolution. The solution is placed under argon and 6.55 g (6.15 mmol, 0.2 eq) of 10% palladium on activated carbon are added carefully. The reaction mixture is heated for 19 h under reflux. After cooling to RT it is filtered over celite. The filtration residue is washed with MeOH and the solvent is removed by means of the rotary evaporator. The crude product is purified by column chromatography (MeOH:EE=1:3). 5.2 g (25.2 mmol, 81%) of a colorless solid is obtained.

$^1$H-NMR (CDCl$_3$, 500 MHz): δ=8.07 (d, J=2.2 Hz, 1H), 7.85 (ddd, J=8.2 Hz, 5.6 Hz, 2.5 Hz, 1H), 6.84 (dd, J=8.5 Hz, 3.0 Hz, 1H), 3.64-3.70 (m, 1H), 3.21 (s, 1H), 3.15 (dd, J=9.3 Hz, 5.0 Hz, 1H), 2.22 (dd, J=13.2 Hz, 9.3 Hz, 1H), 1.50-1.89 (m, 8H).

Example 3

Preparation of (−)-(1R,5S,6S)-6-(6-Fluoro-pyridine-3-yl)-8-aza-bicyclo[3.2.1]octane (V) and (+)-(1S,5R,6R)-6-(6-Fluoro-pyridine-3-yl)-8-aza-bicyclo[3.2.1]octane (VI)

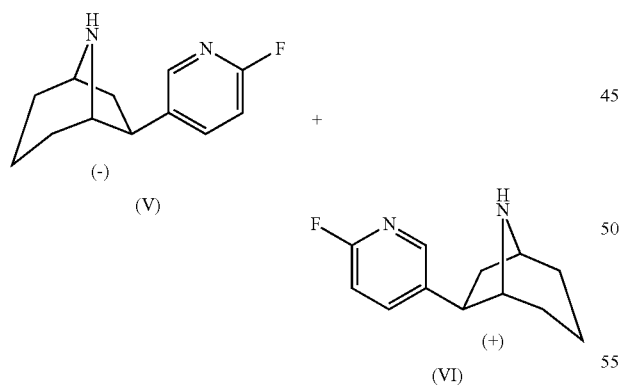

Resolution of racemates is done by semi-preparative chiral HPLC such as e.g. with a 250×20 mm, 5 µL, CHIRALPAK® IA column. 5.2 g (25.2 mmol) of (+/−)-exo-6-(6-fluoro-pyridine-3-yl)-8-aza-bicyclo-[3.2.1]octane-8-carboxylic acid benzyl ester (III) are dissolved in 42 ml of a mobile solvent (MeCN/0.1% diethylamine). The injection volume is 1 ml. Separation was done under isocratic conditions with a flow of 20 ml/min. Detection is performed by means of a UV detector at a wavelength of 280 nm. The retention time of the (+)-enantiomer (VI) is approx. 8-13 min, that of the (−)-enantiomer (V) approx. 19-38 min. Both enantiomers are separately collected, after chiral HPLC the mobile solvent is removed by means of the rotary evaporator. The enantiomeric purity is determined by analytic chiral HPLC by means of a 250×4.6 mm, 5 µL, CHIRALPAK® IA column. 1 mg of the respective enantiomer is dissolved in 1 ml of a mobile solvent (MeOH/0.1% TEA). The injection volume is 10 µL. Separation was done under isocratic conditions with a flow of 1 ml/min. Detection is done at 280 nm. The retention time of the (+)-enantiomer (VI) is 11.5 min, that of the (−)-enantiomer (V) 17.5 min. 2.24 g (10.86 mmol, 43%, >99% ee, [α]$_D^{20}$ (CHCl$_3$, c=0.5)=−30.9°) of (−)-(1R,5S,6S)-6-(6-fluoro-pyridine-3-yl)-8-aza-bicyclo[3.2.1]octane (V) and 2.2 g (10.67 mmol, 42%, >99% ee, [α]$_D^{20}$ (CHCl$_3$, c=0.5)=)+29.0° of (+)-(1S,5R,6R)-6-(6-fluoro-pyridine-3-yl)-8-aza-bicyclo[3.2.1]octane (VI), respectively, is isolated as a colorless solid.

Example 4

Preparation of (−)-(1R,5 S,6S)-[5-(8-Aza-bicyclo[3.2.1]oct-6-yl)-pyridine-2-yl]-dimethylamine(VII-1)

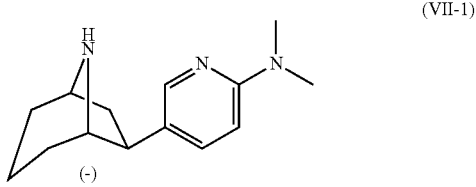 [SMILES: CN(C)c1ccc(C2CC3CCCC2N3)cn1]

1.01 g (4.9 mmol) of (−)-(1R,5S,6S)-6-(6-fluoro-pyridine-3-yl)-8-aza-bicyclo[3.2.1]octane (VI) is dissolved in 49 ml of dimethylamine (5.6M solution in ethanol) and transferred to an autoclave. The autoclave is closed and it is heated for 23 h under stirring to 100° C. After cooling to RT the solvent is removed in vacuo. The residue is purified by column chromatography (EE:MeOH:TEA=9:1:0.1). 0.95 g (4.25 mmol, 86%) of a colorless solid is obtained.

$^1$H-NMR (CDCl$_3$, 500 MHz): δ=8.03 (d, J=2.4 Hz, 1H), 7.45 (dd, J=8.8 Hz, 2.5 Hz, 1H), 6.49 (dd, J=8.8 Hz, 3.0 Hz, 1H), 3.60-3.67 (m, 1H), 3.26 (bs, 1H), 3.07 (dd, J=9.2 Hz, 5.1 Hz, 1H), 3.05 (s, 6H), 2.18 (dd, J=13.2 Hz, 9.2 Hz, 1H), 1.57-1.91 (m, 7H), 1.46-1.54 (m, 1H).

Example 5

Preparation of (−)-(1R,5S,6S)-6-(6-Dimethylamino-pyridine-3-yl)-8-aza-bicyclo[3.2.1]octane-8-carboxylic acid tert.-butyl ester (VIII-1)

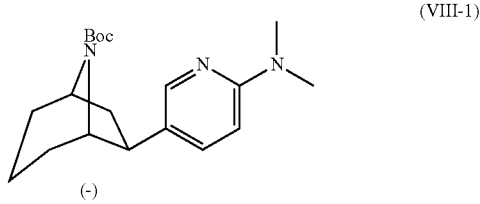 [SMILES: CN(C)c1ccc(C2CC3CCCC2N3C(=O)OC(C)(C)C)cn1]

0.95 g (4.25 mmol, 1 eq) of (−)-(1R,5S,6S)-[5-(8-aza-bicyclo[3.2.1]oct-6-yl)-pyridine-2-yl]-dimethylamine (VII-1) is dissolved in 140 ml of THF. The dropwise addition of 0.86 ml (6.17 mmol, 1.45 eq) of TEA is followed by the addition of a solution of 1.35 g (6.18 mmol, 1.45 eq) of di-tert-butyldicarbonate in 10.5 ml THF. The solution is stirred for 4 h at RT before the solvent is removed by means of the rotary evaporator. The crude product is purified by column chromatography (EE:Hex=1:2). 1.34 g (4.04 mmol, 95%) is obtained as a colorless solid.

$^1$H-NMR (CDCl$_3$, 500 MHz) two rotameric forms (RotA/RotB) result in a doubling of some signals: δ=7.94-8.02 (m, 1H, RotA, 1H, RotB), 7.29-7.38 (m, 1H, RotA, 1H, RotB), 6.47 (d, J=8.8 Hz, 1H, RotA, 1H, RotB), 4.41 (bd, J=7.1 Hz, 1H, RotA), 4.27 (bd, J=7.0 Hz, 1H, RotB), 4.08 (bs, 1H, RotB), 3.96 (bs, 1H, RotA), 3.00 (m, 1H. RotA. 1H RotB). 3.05 (s, 6H, RotA), 3.04 (s, 6H, RotB), 2.15-2.26 (m, 1H, RotB), 2.19 (dd, J=12.6 Hz, 9.5 Hz, 1H, RotA), 1.40-1.98 (m, 7H, RotA, 7H, RotB), 1.50 (s, 9H, RotA), 1.45 (s, 9H, RotB).

Example 6

Preparation of (−)-(1R,5S,6S)-5-(8-tert-Butoxycarbonyl-8-aza-bicyclo[3.2.1]oct-6-yl)-N,N,N-trimethylpyridine-2-aminium iodide (Ia-1)

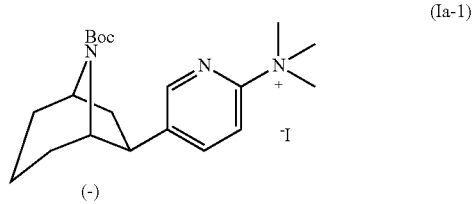

(Ia-1)

(−)

1.34 g (4.04 mmol, 1 eq) of (−)-(1R,5S,6S)-6-(6-dimethylamino-pyridine-3-yl)-8-aza-bicyclo[3.2.1]octane-8-carboxylic acid tert.-butyl ester (VIII-1) are dissolved under argon in 12.9 ml of MeOH. 25.1 ml (404 mmol, 100 eq) methyl iodide and 20.8 g (150.5 mmol, 37.5 eq) of potassium carbonate are successively added. The reaction flask is closed with a glass stopper and stirred under light exclusion for 5 d at RT. After this time it is diluted with 130 ml DCM and filtered. The filtrate is concentrated in vacuo to small volume, dissolved in 70 ml of EE and quickly filtered over a syringe filter. The solvent is removed by means of a rotary evaporator. To the residue 100 ml diethyl ether was added and intensively stirred for 1 h. The precipitate is sucked off over a frit and washed three times with diethyl ether. The crude product is suspended in 50 ml of diethyl ether and laced with 10 ml of DCM. After stirring for 1 h at RT the precipitate is sucked off and washed three times with diethyl ether. 1.34 g (2.83 mmol, 70%) of a colorless solid is obtained.

$^1$H-NMR (CDCl$_3$, 500 MHz) two rotameric forms (RotA/RotB) result in a doubling of some signals: δ=8.37 (d, J=2.1 Hz, 1H, RotA, 1H, RotB), 8.29 (d, J=8.0 Hz, 1H, RotB), 8.28 (d, J=8.4 Hz, 1H, RotA), 7.92 (dd, J=8.6 Hz, J=1.9 Hz, 1H, RotA, 1H, RotB), 4.45 (bd, J=7.0 Hz, 1H, RotB), 4.35 (bd, J=6.9 Hz, 1H, RotA), 4.10 (bs, 1H, RotA), 4.06 (bs, 1H, RotB), 3.97 (s, 9H, RotB), 3.95 (s, 9H, RotA), 3.27-3.34 (m, 1H, RotB), 3.30 (dd, J=9.1 Hz, 4.6 Hz, 1H, RotA), 2.28-2.38 (m, 1H, RotA, 1H, RotB), 1.98-2.08 (m, 1H, RotA), 1.41-1.97 (m, 6H, RotA, 7H, RotB), 1.50 (s, 9H, RotA), 1.48 (s, 9H, RotB); [α]$_D^{20}$ (CHCl$_3$, c=0.5)=−47.4°; elemental analysis—calculated: C, 50.74; H, 6.81; N, 8.88; I, 26.81. found: C, 49.88; H, 6.65; N, 8.68, I26.79.

Example 7

Preparation of (+6-(6-Dimethylamino-pyridine-3-yl)-8-aza-bicyclo[3.2.1]octane-8-carboxylic acid-9H-fluorene-9-ylmethyl ester (VIII-2)

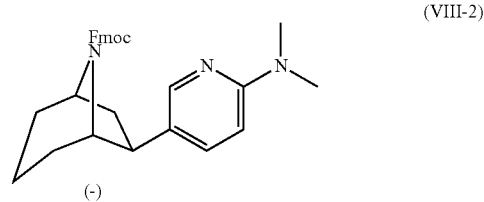

(VIII-2)

(−)

219 mg (0.95 mmol, 1 eq) of (−)-[5-(8-aza-bicyclo[3.2.1]oct-6-yl)-pyridine-2-yl]-dimethylamine (VII-1) are dissolved in 1.8 ml of dioxane and 2.75 ml of 10% sodium carbonate solution. 257 mg (1 mmol, 1.05 eq) of Fmoc-Cl in portions is added and it is stirred for 1 h at RT. After this time it is diluted with EE and washed with water. The aqueous phase is re-extracted for three times with EE. The combined organic phases are dried over sodium sulphate and the solvent is removed in vacuo. The crude product is purified by column chromatography (EE:hex=1:2). 422 mg (0.93 mmol, 98%) of a colorless foam/solid is obtained.

$^1$H-NMR (CDCl$_3$, 500 MHz) two rotameric forms (RotA/RotB) result in the doubling of some signals: δ=8.02 (d, J=2.3 Hz, 1H, RotA), 7.98 (d, J=2.2 Hz, 1H, RotB), 7.78 (bd, J=7.6 Hz, 2H, RotB), 7.73 (d, J=7.5 Hz, 2H, RotA), 7.64 (bd, J=6.6 Hz, 2H, RotB), 7.53 (d, J=7.5 Hz, 1H, RotA), 7.47 (d, J=7.5 Hz, 1H, RotA), 7.17-7.43 (m, 5H, RotA, 5H, RotB), 6.46 (d, J=8.8 Hz, 1H, RotB), 6.45 (d, J=8.8 Hz, 1H, RotA), 4.44-4.56 (m, 2H, RotA, 2H, RotB), 4.38 (dd, J=10.6 Hz, 7.3 Hz, 1H, RotA), 4.34 (bd, J=7.2 Hz, 1H, RotB), 4.28 (t, J=6.6 Hz, 1H, RotB), 4.21 (t, J=6.9 Hz, 1H, RotA), 4.15 (bs, 1H, RotB), 4.07 (bs, 1H, RotA), 3.14 (dd, J=9.3 Hz, 4.7 Hz, 1H, RotA), 3.09 (dd, J=9.3 Hz, 4.8 Hz, 1H, RotB), 3.05 (s, 6H, RotA), 3.04 (s, 6H, RotB), 2.19-2.29 (m, 1H, RotA, 1H, RotB), 1.73-2.03 (m, 3H, RotA, 3H, RotB), 1.55-1.70 (m, 3H, RotA, 3H, RotB), 1.40-1.53 (m, 1H, RotA, 1H, RotB).

Example 8

Preparation of (−)-{5-[8-(9H-Fluorene-9-ylmethoxycarbonyl)-8-aza-bicyclo[3.2.1]oct-6-yl]-pyridine-2-yl}-N,N,N-trimethylpyridine-2-aminium iodide (Ia-2)

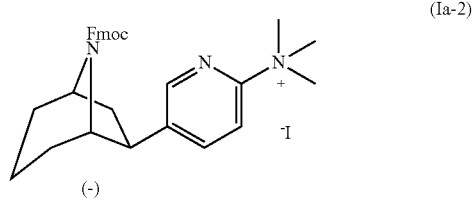

(Ia-2)

(−)

137 mg (0.3 mmol, 1 eq) of (−)-6-(6-dimethylamino-pyridine-3-yl)-8-aza-bicyclo[3.2.1]octane-8-carboxylic acid-9H-fluorene-9-ylmethyl ester (VIII-2) are dissolved under argon in 1 ml of DCM. 1.88 ml (30.2 mmol, 100 eq)

of methyl iodide is added. The reaction flask is closed with a glass stopper and stirred under light exclusion for 4 d at RT. The solvent is removed by means of the rotary evaporator. The residue is laced with diethyl ether and intensively stirred for 1 h. The precipitate is sucked off over a frit and washed for three times with diethyl ether. 166 mg (0.28 mmol, 92%) of a pale yellow solid is obtained.

$^1$H-NMR (DMSO-D$_6$, 500 MHz): δ=8.42 (s, 1H), 7.78-8.08 (m, 4H), 7.17-7.75 (m, 6H), 4.38-4.65 (m, 2H), 4.03-4.36 (m, 2H), 3.82-3.99 (m, 1H), 3.30-3.79 (m, 10H), 2.15-2.34 (m, 1H), 1.69-2.01 (m, 2H), 1.17-1.66 (m, 5H).

Example 9

Preparation of (−)-Dimethyl-[5-(8-trityl-8-aza-bicyclo[3.2.1]oct-6-yl)-pyridine-2-yl]-amine (VIII-3)

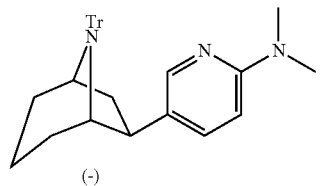

(VIII-3)

(−)

217 mg (0.94 mmol, 1 eq) of (−)-[5-(8-aza-bicyclo[3.2.1]oct-6-yl)-pyridine-2-yl]-dimethylamine (VII-1) are dissolved in 1 ml of chloroform. 195 μL (1.4 mmol, 1.5 eq) of TEA and 274 mg (0.98 mmol, 1.05 eq) of tritylchloride are added. After stirring for 1 and 2.5 h at RT 195 μL (1.4 mmol, 1.5 eq) of TEA and 274 mg (0.98 mmol, 1.05 eq) of tritylchloride are added. After stirring for a total of 4 h at RT it is diluted with EE. It is washed once with water, the aqueous phase is re-extracted twice with EE. The combined organic phases are dried over sodium sulphate and the solvent is removed in vacuo. The crude product is purified by column chromatography (EE:hex=1:3). 158 mg (0.33 mmol, 35%) of a colorless foam is obtained.

$^1$H-NMR (CDCl$_3$, 500 MHz): δ=7.47 (bs, 1H), 7.40-7.50 (m, 3H), 7.21-7.35 (m, 6H), 6.97-7.07 (m, 6H), 6.77 (dd, J=8.6 Hz, 1.7 Hz, 1H), 6.30 (d, J=8.7 Hz, 1H), 4.09 (s, 1H), 3.75 (bd, J=5.4 Hz, 1H), 3.27 (t, J=8.6 Hz, 1H), 3.05 (s, 6H), 2.41-2.50 (m, 1H), 2.19-2.29 (m, 1H), 1.74-1.94 (m, 2H), 1.78 (dd, J=12.3 Hz, 9.6 Hz, 1H), 1.65-1.74 (m, 1H), 1.48 (dd, J=12.1 Hz, 6.0 Hz, 1H), 1.35-1.43 (m, 1H).

Example 10

Preparation of (−)-N,N,N-Trimethyl-[5-(8-trityl-8-aza-bicyclo[3.2.1]oct-6-yl)-pyridine-2-yl]-pyridine-2-aminium iodide (Ia-3)

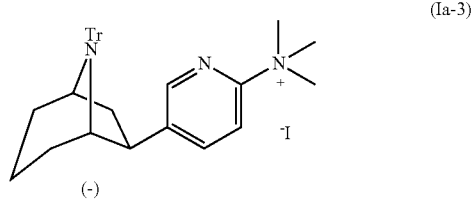

(Ia-3)

(−)

125 mg (0.26 mmol, 1 eq) of (−)-dimethyl-[5-(8-trityl-8-aza-bicyclo[3.2.1]oct-6-yl)-pyridine-2-yl]-amine are dissolved under argon in 0.85 ml MeOH. 1.6 ml (26.4 mmol, 100 eq) of methyl iodide and 1.37 g (9.9 mmol, 37.5 eq) of potassium carbonate are successively added. The reaction flask is closed with a glass stopper and stirred under light exclusion for 5 d at RT. After this time it is diluted with DCM and filtered. The filtrate is concentrated in vacuo to small volume. The residue is laced with diethyl ether and intensively stirred for 1 h. The precipitate is sucked off over a frit and washed with diethyl ether for three times. The crude product is suspended in 3 ml of diethyl ether and laced with 1 ml of DCM. After stirring for 1 h at RT the precipitate is sucked off and washed with diethyl ether for three times. 74.6 mg (0.12 mmol, 45%) of a colorless solid is obtained.

$^1$H-NMR (DMSO-D$_6$, 500 MHz): δ=7.62-7.78 (m, 2H), 7.20-7.53 (m, 6H), 7.44 (d, J=8.0 Hz, 1H), 6.93-7.17 (m, 9H), 4.07 (s, 1H), 3.74 (bs, 1H), 3.57 (s, 9H), 3.26-3.44 (m, 1H), 2.41-2.56 (m, 1H), 2.19-2.31 (m, 1H), 1.76-1.94 (m, 4H), 2.48-1.62 (m, 2H).

Example 11

Radiosynthesis of the Enantiomerically Pure (−)-[$^{18}$F]NCFHEB (IXa)

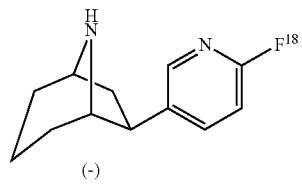

(IXa)

(−)

Example 11a

Radiosynthesis of (−)-[$^{18}$F]NCFHEB Starting with (−)-(1R,5S,6S)-5-(8-tert-Butoxycarbonyl-8-aza-bicyclo[3.2.1]oct-6-yl)-N,N,N-trimethylpyridine-2-aminium iodide (Ia-1)

100-300 μl of aqueous [$^{18}$F]fluoride solutions [activity: 10 MBq-2 GBq] are directly transferred to MeCN, wherein 10 mg (0.0266 mmol) to 25 mg (0.0664 mmol) of Kryptofix and analogically 1.8 mg (0.0136 mmol) to 4.59 mg (0.0332 mmol) of potassium carbonate are dissolved. After complete withdrawal of the solvent, short-time cooling of the reaction vessel, and repeated addition of 0.5-1 ml of MeCN the PTC complex is produced in the closed reaction vessel after heating to 75-80° C. within 2-3 min. After addition of 0.5-1.0 mg (0.237-0.473 mmol) of (−)-(1R,5S,6S)-5-(8-tert-butoxycarbonyl-8-aza-bicyclo[3.2.1]oct-6-yl)-N,N,N-trimethylpyridine-2-aminium iodide (Ia-1) in 1 ml MeCN to the K[$^{18}$F]F-K222 carbonate complex and heating to boiling heat a labeling yield of about 88% is obtained after a reaction time of 30 minutes. For deprotection 1 ml of 1M HCl or 1M H$_3$PO$_4$ is added to the present reaction solution. Heating to 90° C. results in the complete cleavage of the Boc protective group after 5 to 10 min. Subsequently, the reaction solutions are neutralized by the addition of aqueous, preferably 1M NaOH or saturated NaHCO$_3$ solution (preferably also the use of a Pfrimmer's solution). The collected fractions of (−)-[$^{18}$F]NCFHEB (1-3 ml) are diluted in 25 ml water and stirred over an RP-18 cartridge (SEP-Pak C18 Plus, Waters US) within 5-8 min at constant pressure. The cartridge is conditioned (5 ml EtOH, 5 ml water, purging) shortly before its use according to common methods. As a rule, during application the quantitative fixation of the (−)-[$^{18}$F]NCFHEB takes place. In order to remove residues of solvents the cartridge is purged by means of air or an inert gas (2-4 min), subsequently washed with 2-5 ml of water and again treated with air or an inert gas. This is followed by the elution with absolute ethanol, wherein as a rule a main fraction of 1.5 ml of (−)-[$^{18}$F]NCFHEB in total is isolated.

Alternatively, cartridges with an acidic cationic exchanger, preferably with combined RP and cation exchange function may be used. Application to the cartridges is performed in the same way; moreover, the EtOH containing eluent contains selected additives of acids, salts, or bases.

The product batch (1 ml MeCN) is diluted with 3 ml of water and for resolution subjected to a semi-preparative HPLC system. Resolution takes place in an RP phase. Column: Multospher 120 RP18 AQ-5, 150×10 mm, 5 µm particle size (CS Chromatographie Service, Germany). Eluent: 25% MeCN+20 mM NH$_4$OAc, 1 ml/min. $t_R$ [(−)-[$^{18}$F]NCFHEB]: ~22 min, total yield >70%.

For the subsequent sterile filtration filters of a pore diameter of 0.22 µm, preferably sterile disposable material, and/or filters with simultaneous retention of endotoxin are used.

To formulate a solution for intravenous injection the solution obtained after sterile filtration is transferred to a sterile final vessel which, i.a. contains a corresponding amount of suitable saline solution to adjust a defined osmolality. The transferred portion of ethanol in the final solution should be between 0.1 and 1% and stabilizes the product against radiolysis.

Example 11b

Radiosynthesis of (−)-[$^{18}$F]NCFHEB Starting with (−)-(1R,5S,6S)-5-(8-tert-butoxycarbonyl-8-aza-bicyclo[3.2.1]oct-6-yl)-N,N,N-trimethylpyridine-2-aminium iodide (Ia-1) Under Microwave Conditions 0.5-1.0 mg (0.237-0.473 mmol) of (−)-(1R,5S,6S)-5-(8-tert-butoxycarbonyl-8-aza-bicyclo[3.2.1]oct-6-yl)-N,N,N-trimethylpyridine-2-aminium iodide (Ia-1) are dissolved in extra dry solvent, added to the K[$^{18}$F]F-K222 carbonate complex and reacted at approx. 75 W/70-80° C. (MeCN) and approx. 85 W/110-120° C. (DMSO), respectively. After 1, 2, 3, and 5 min approx. 85 and 75% labeling yield, respectively, is constantly obtained.

Example 11c

Radiosynthesis of (−)-[$^{18}$F]NCFHEB Starting with (−)-N,N,N-Trimethyl-[5-(8-trityl-8-aza-bicyclo[3.2.1]oct-6-yl)-pyridine-2-yl]-pyridine-2-aminium iodide (Ia-3)

4-6 mg of (−)-N,N,N-Trimethyl-[5-(8-trityl-8-aza-bicyclo[3.2.1]oct-6-yl)-pyridine-2-yl]-pyridine-2-aminium iodide (Ia-3) is added to the described K[$^{18}$F]F-K222 carbonate complex. Labeling is carried out in 1 ml of MeCN at boiling heat. After reaction times of 15 to 20 min constant reaction yields of 16-18% of the radio-fluorinated intermediate and several $^{18}$F labeled by-products are obtained.

Reaction in other solvents such as DMF and DMSO as well as the use of other PTC results in lower or only slightly higher labeling yields. Deprotection of the trityl-protected intermediate is done in the reaction batch (1 ml MeCN) by addition of 1 ml of 1M HCl, wherein a conversion of 55-65% is reached after 20 min, preferably by addition of 1 ml of 1M H$_3$PO$_4$ at 85-90° C., wherein 80-85% is reached after 10 min. Thus, for radiosynthesis with (−)-N,N,N-trimethyl-[5-(8-trityl-8-aza-bicyclo[3.2.1]oct-6-yl)-pyridine-2-yl]-pyridine-2-aminium iodide (Ia-3) only 10-14% total yield (−)-[$^{18}$F]NCFHEB is obtained.

Example 11d

Radiosynthesis of (−)-[$^{18}$F]NCFHEB Starting with (−)-{5-[8-(9H-Fluorene-9-ylmethoxycarbonyl)-8-aza-bicyclo[3.2.1]oct-6-yl]-pyridine-2-yl}-N,N,N-trimethylpyridine-2-aminium iodide (Ia-2)

2.5-3 mg of (−)-{5-[8-(9H-Fluorene-9-ylmethoxycarbonyl)-8-aza-bicyclo[3.2.1]oct-6-yl]-pyridine-2-yl}-N,N,N-trimethylpyridine-2-aminium iodide (Ia-2) is added to the K[$^{18}$F]F-K222 carbonate complex. The reaction is carried out in 1 ml of MeCN at boiling heat. After reaction times of approx. 30 min constant reaction yields of 20-25% of the radio-fluorinated intermediate as well as several $^{18}$F by-products are obtained. A small extent (2-4%) of spontaneous deprotection to (−)-[$^{18}$F]NCFHEB is observed; the cause is the weakly basic milieu. Reaction in other solvents such as DMF and DMSO as well as the use of other PTC resulted in comparable or lower yields. Deprotection of the Fmoc-protected intermediate is done in the reaction batch (1 ml of MeCN) by addition of 1 ml of 1M NaOH at 85-90° C., wherein after a very long reaction time of about 60 min the target product (−)-[$^{18}$F]NCFHEB is formed almost quantitatively (93-98%). For the radiosynthesis with the Fmoc precursor (Ia-2) a total yield of only 18-24% of (−)-[$^{18}$F]NCFHEB is obtained.

Example 12

Thin Layer Chromatography

The radiochemical purity and the content of non-radioactive components can be determined by means of thin layer chromatography as described in the following example.

Sorbent on carrier, preferably silica gel G 60 with fluorescence indicator F254 (SIL G/UV$_{254}$), mobile solvent MTBE/TEA 92:8 (v/v), rising development in a closed TLC chamber, assessment of the radio TLC band: Rf (−)-[$^{18}$F]NCFHEB 0.27; Rf (−)-[$^{18}$F]Boc intermediate; 0.83; Rf (−)-[$^{18}$F]Fmoc intermediate 0.75; Rf (−)-[$^{18}$F]trityl intermediate 0.88.

Example 13

Analytical HPLC

Alternatively, the radiochemical purity and the content of non-radioactive components can be determined by analytical HPLC on RP phases.

Column 1: Multospher 120 RP18 AQ-5, 250×4.6 mm, 5 µm particle size (CS Chromatographie Service, Germany). Eluent gradient: 5% MeCN (0-5 min), 5% to 40% (5-40 min), 40% MeCN+20 mM NH$_4$OAc (40-50 min), 1 ml/min, $t_R$ (−)-[$^{18}$F]NCFHEB ~35 min.

The is claimed is:
1. A compound of formula Ia or Ib

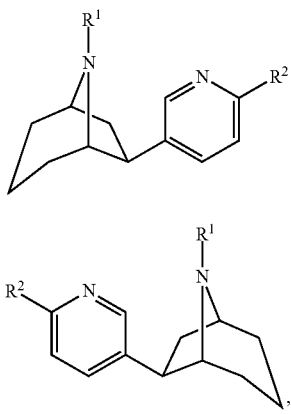

wherein
R$^1$ represents —CO$_2$R$^3$, —COR$^4$ or —R$^5$, wherein
R$^3$ represents unsubstituted or substituted C$_1$-C$_6$ alkyl,
R$^4$ represents hydrogen, unsubstituted or substituted C$_1$-C$_6$ alkyl, and
R$^5$ represents hydrogen, unsubstituted or substituted C$_1$-C$_6$ alkyl,
R$^2$ represents —N$^+$(R$^6$)(R$^7$)(R$^8$)X$^-$ or nitro, wherein
R$^6$, R$^7$, R$^8$ independently of each other represent unsubstituted or substituted C$_1$-C$_6$ alkyl or unsubstituted or substituted —(CH2)$_n$— with n=1 to 12 provided that at least two of the substituents R$^6$, R$^7$, and R$^8$ are C$_1$-C$_6$ alkyl, and
X$^-$ represents a halide, sulphonate, unsubstituted or substituted acetate, sulphate, hydrogen sulphate, nitrate, perchlorate, or oxalate.
2. The compound of claim 1, wherein
R$^3$ is selected from the group consisting of methyl, ethyl, tert-butyl, (9H -fluorenyl)methyl, allyl, and benzyl; and/or
R$^4$ is selected from the group consisting of hydrogen, methyl, and trifluoromethyl; and/or
R$^5$ is selected from the group consisting of benzyl, methoxybenzyl, dimethoxybenzyl, allyl, diphenyl, and trityl; and/or
R$^6$, R$^7$, R$^8$ independently are selected from the group consisting of methyl, ethyl, and tert-butyl; and/or
X$^-$ is selected from the group consisting of chloride, bromide, iodide, mesylate, and triflate.
3. The compound of claim 1, wherein
R$^3$ represents tert-butyl;
R$^4$ represents methyl;
R$^5$ represents trityl;
R$^6$, R$^7$, R$^8$ represent methyl; and
X$^-$ represents iodide.
4. (−)-5-(8-(tert-Butoxycarbonyl)-8-azabicyclo[3.2.1]octane-6-yl)-N,N,N-tri-methylpyridine-2-aminium iodide.
5. A method for the preparation of a compound of formula Ia

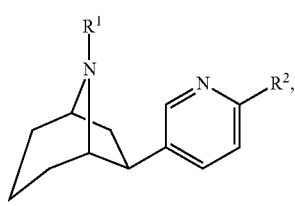

wherein:
R$^4$ represents —CO$_2$R$^3$, —COR$^4$ or —R$^5$, wherein
R$^3$ represents unsubstituted or substituted C$_1$-C$_6$ alkyl,
R$^4$ represents hydrogen, unsubstituted or substituted C$_1$-C$_6$ alkyl, and
R$^5$ represents hydrogen, unsubstituted or substituted C$_1$-C$_6$ alkyl,
R$^2$ represents —N+(R$^6$)(R$^7$)(R$^8$)X$^-$ or nitro, wherein
R$^6$, R$^7$, R$^8$ independently of each other represent unsubstituted or substituted C$_1$-C$_6$ alkyl or unsubstituted or substituted —(CH$_2$)$_n$— with n=1 to 12 provided that at least two of the substituents R$^6$, R$^7$, and R$^8$ are C$_1$-C$_6$ alkyl, and
X$^-$ represents a halide, sulphonate, unsubstituted or substituted acetate, sulphate, hydrogen sulphate, nitrate, perchlorate, or oxalate.
wherein the method comprises:
the reaction of a compound of formula II with 2-fluoro-5-iodopyridine using a palladium catalyst

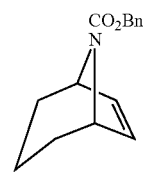

to a compound of formula III

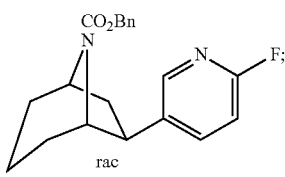

the cleavage of the protective group in a compound of formula III with hydrogen using a palladium catalyst to obtain a compound of formula (IV)

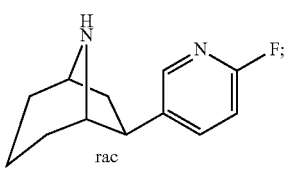

an enantiomeric separation of the compound of formula IV to obtain compounds of formula V and/or of formula VI

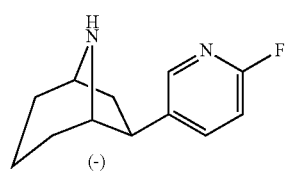

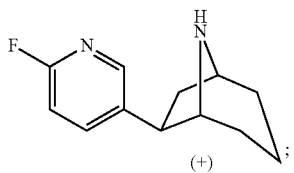

(+) ;

and the substitution of the fluorine in a compound of formula V with a dialkylamine to obtain a compound of formula VII

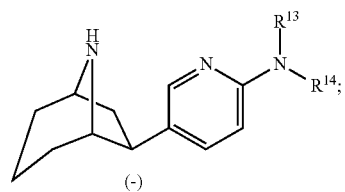

(-)

wherein $R^{13}$ and $R^{14}$ are independently selected from the group consisting of methyl, ethyl, and tert-butyl, the introduction of a protective group into the compound of formula VII to obtain a compound of formula VIII

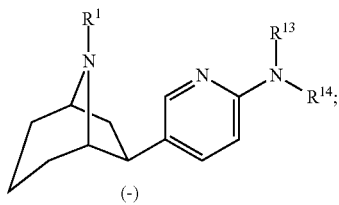

(-)

and the quaternization of the compound of formula VIII with an alkylating agent to a compound of formula Ia.

* * * * *